(12) United States Patent
Meade et al.

(10) Patent No.: US 6,608,054 B2
(45) Date of Patent: Aug. 19, 2003

(54) PHARMACEUTICAL COMPOSITIONS BASED ON ANTICHOLINERGICS AND ENDOTHELIN ANTAGONISTS

(75) Inventors: Christopher J. M. Meade, Bingen (DE); Michel Pairet, Stromberg (DE); Michael P. Pieper, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/100,659

(22) Filed: Mar. 18, 2002

(65) Prior Publication Data

US 2002/0183347 A1 Dec. 5, 2002

Related U.S. Application Data

(60) Provisional application No. 60/281,874, filed on Apr. 5, 2001.

(30) Foreign Application Priority Data

Mar. 20, 2001 (DE) .......................... 101 13 366

(51) Int. Cl.[7] ...................... A61K 31/535; A61K 31/42; A61K 31/255
(52) U.S. Cl. .................... 514/229.5; 514/374; 514/378; 514/518; 514/826
(58) Field of Search .............................. 514/229.5, 374, 514/378, 518, 826

(56) References Cited

U.S. PATENT DOCUMENTS 6,197,824 B1 * 3/2001 Schromm et al. ........... 514/637
6,433,027 B1 * 8/2002 Bozung et al. ............. 514/826
6,455,524 B1 * 9/2002 Bozung et al. .......... 514/229.5

FOREIGN PATENT DOCUMENTS

WO  WO96/13292 A  5/1996

OTHER PUBLICATIONS

Budavari et al., The Merck Index, Twelfth Edition (1996), p. 1614, abstract No. 9598.*
Takahashi et al., "Contraction of human airway smooth muscle by endothelin–1 and IRL 1620: effect of bosentan", European Journal of Pharmacology (1997), 324(2,3), p. 219–222 (see the abstract).*
D. W. P. Hay: "Chronic obstructive pulmonary disease: emerging therapies" Current Opinion in Chemical Biology, Bd. 4, Nr. 4, 2000, pp. 412–419.

* cited by examiner

Primary Examiner—Kevin E. Weddington
(74) Attorney, Agent, or Firm—Robert P. Raymond; Mary-Ellen M. Devlin; Alan R. Stempel (57) ABSTRACT

The present invention relates to novel pharmaceutical compositions based on anticholinergics and endothelin antagonists, processes for preparing them and their use in the treatment of respiratory tract diseases.

9 Claims, 3 Drawing Sheets

PHARMACEUTICAL COMPOSITIONS BASED ON ANTICHOLINERGICS AND ENDOTHELIN ANTAGONISTS

BACKGROUND OF THE INVENTION

The present invention relates to novel pharmaceutical compositions based on anticholinergics and endothelin antagonists, processes for preparing them and their use in the treatment of respiratory diseases.

BRIEF DESCRIPTION OF THE INVENTION

The present invention relates to novel pharmaceutical compositions based on anticholinergics and endothelin antagonists, processes for preparing them and their use in the treatment of respiratory diseases.

Surprisingly, it has been found that an unexpectedly beneficial therapeutic effect, particularly a synergistic effect can be observed in the treatment of diseases of the upper or lower respiratory tract, particularly in the treatment of allergic or non-allergic rhinitis, if one or more, preferably one anticholinergic is or are used together with one or more, preferably one, endothelin antagonist. Thanks to this synergistic effect the pharmaceutical combinations according to the invention can be used in lower doses than is the case when the individual compounds are used in monotherapy in the usual way.

The effects mentioned above are observed both when the two active substances are administered simultaneously in a single active substance formulation and when they are administered successively in separate formulations. According to the invention, it is preferable if the two active substance ingredients are administered simultaneously in a single formulation.

Within the scope of the present invention the term anticholinergics 1 denotes salts which are preferably selected from the group consisting of tiotropium salts, oxitropium salts and ipratropium salts, of which ipratropium salts and tiotropium salts are particularly preferred. In the abovementioned salts the cations tiotropium, oxitropium and ipratropium are the pharmacologically active ingredients. Within the scope of the present patent application, any reference to the above cations is indicated by the use of the number 1'. Any reference to compounds 1 naturally also includes a reference to the ingredients 1' (tiotropium, oxitropium or ipratropium).

By the salts 1 which may be used within the scope of the present invention are meant the compounds which contain, in addition to tiotropium, oxitropium or ipratropium, as counter-ion (anion), chloride, bromide, iodide, methanesulphonate or para-toluenesulphonate. Within the scope of the present invention, the methanesulphonate, chloride, bromide and iodide are preferred of all the salts 1, the methanesulphonate and bromide being of particular importance. Salts 1 selected from among tiotropium bromide, oxitropium bromide and ipratropium bromide are of outstanding importance according to the invention. Ipratropium bromide and tiotropium bromide are particularly preferred.

Within the scope of the present invention the term endothelin antagonists (hereinafter 2) denotes compounds selected from among tezosentan, bosentan, enrasentan, sixtasentan, T-0201, BMS-193884, K-8794, PD-156123, PD-156707, PD-160874, PD-180988, S-0139 and ZD-1611. Preferred endothelin antagonists 2 within the scope of the present invention are those selected from among tezosentan, bosentan, enrasentan, sixtasentan, T-0201 and BMS-193884, the compounds tezosentan and bosentan being particularly preferred according to the invention.

Any reference to the abovementioned endothelin antagonists 2 within the scope of the present invention includes a reference to any pharmacologically acceptable acid addition salts thereof which may exist. By the physiologically or pharmacologically acceptable acid addition salts which may be formed from 2 are meant, according to the invention, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid.

Any reference to the abovementioned endothelin antagonists 2 within the scope of the present invention includes a reference to any alkali metal and alkaline earth metal salts thereof which may exist. If the compounds of formula 2 are present in the form of their basic salts, the sodium or potassium salts are particularly preferred.

The pharmaceutical combinations of 1 and 2 according to the invention are preferably administered by parenteral or oral route or by inhalation, the latter being particularly preferred. For oral or parenteral administration the pharmaceutical compositions according to the invention may be administered in the form of solutions and tablets. For inhalation, as preferred according to the invention, suitable inhalable powders may be used which are packed into suitable capsules (inhalettes) and administered using suitable powder inhalers. Alternatively, the drug may be inhaled by the application of suitable inhalation aerosols. These include inhalation aerosols which contain HFA134a, HFA227 or a mixture thereof as propellant gas. The drug may also be inhaled using suitable solutions of the pharmaceutical combination consisting of 1 and 2.

In one aspect, therefore, the invention relates to a pharmaceutical composition which contains a combination of 1 and 2.

In another aspect the present invention relates to a pharmaceutical composition which contains one or more salts 1 and one or more compounds 2, optionally in the form of their solvates or hydrates. The active substances may either be combined in a single preparation or contained in two separate formulations. Pharmaceutical compositions which contain the active substances 1 and 2 in a single preparation are preferred according to the invention.

In another aspect the present invention relates to a pharmaceutical composition which contains, in addition to therapeutically effective quantities of 1 and 2, a pharmaceutically acceptable carrier or excipient. In another aspect the present invention relates to a pharmaceutical composition which does not contain any pharmaceutically acceptable carrier or excipient in addition to therapeutically effective quantities of 1 and 2.

The present invention also relates to the use of 1 and 2 for preparing a pharmaceutical composition containing therapeutically effective quantities of 1 and 2 for treating diseases of the upper or lower respiratory tract, particularly for treating asthma, chronic obstructive pulmonary diseases (COPD) and/or pulmonary hypertension, as well as allergic and non-allergic rhinitis, provided that treatment with endothelin antagonists is not contraindicated from a therapeutic point of view, by simultaneous or successive administration. The present invention preferably relates to the abovementioned use of 1 and 2 for preparing a pharmaceutical composition containing therapeutically effective quantities of 1 and 2 for treating asthma and/or chronic obstructive pulmonary diseases (COPD), which may possibly be associated with pulmonary hypertension, as well as allergic and non-allergic rhinitis, provided that treatment with endothelin antagonists is not contraindicated from a therapeutic point of view, by simultaneous or successive administration. Of equal importance is the abovementioned use of 1 and 2 for preparing a pharmaceutical composition containing therapeutically effective quantities of 1 and 2 for treating pulmonary hypertension.

The present invention further relates to the simultaneous or successive use of therapeutically effective doses of the combination of the above pharmaceutical compositions 1 and 2 for treating inflammatory or obstructive diseases of the respiratory tract, particularly asthma, chronic obstructive pulmonary diseases (COPD) and/or pulmonary hypertension, as well as allergic and non-allergic rhinitis, provided that treatment with endothelin antagonists is not contraindicated from a therapeutic point of view, by simultaneous or successive administration. The present invention preferably relates to the abovementioned use of therapeutically effective doses of the combination of the abovementioned pharmaceutical compositions 1 and 2 for treating asthma and/or chronic obstructive pulmonary diseases (COPD), which may possibly be associated with pulmonary hypertension, as well as allergic and non-allergic rhinitis, provided that treatment with endothelin antagonists is not contraindicated from a therapeutic point of view, by simultaneous or successive administration. Of equal importance is the abovementioned use of therapeutically effective doses of the combination of the abovementioned pharmaceutical compositions 1 and 2 for treating pulmonary hypertension.

In the active substance combinations of 1 and 2 according to the invention, ingredients 1 and 2 may be present in the form of their enantiomers, mixtures of enantiomers or in the form of racemates.

DETAILED DESCRIPTION OF THE INVENTION

The proportions in which the two active substances 1 and 2 may be used in the active substance combinations according to the invention are variable. Active substances 1 and 2 may possibly be present in the form of their solvates or hydrates. Depending on the choice of the compounds 1 and 2, the weight ratios which may be used within the scope of the present invention vary on the basis of the different molecular weights of the various compounds and their different potencies. As a rule, the pharmaceutical combinations according to the invention may contain compounds 1 and 2 in ratios by weight ranging from 1:300 to 50:1, preferably from 1:250 to 40:1. In the particularly preferred pharmaceutical combinations which contain ipratropium salt or tiotropium salt as compound 1 and a compound selected from among tezosentan, bosentan, enrasentan, sixtasentan, T-0201 and BMS-193884 as endothelin antagonist 2, the weight ratios of 1 to 2 are most preferably in a range in which ipratropium or tiotropium 1' and 2 are present in proportions of 1:150 to 30:1, more preferably from 1:50 to 20:1.

For example, without restricting the scope of the invention thereto, preferred combinations of 1 and 2 according to the invention may contain ipratropium or tiotropium 1' and endothelin antagonist 2 in the following weight ratios: 1:80; 1:79; 1:78; 1:77; 1:76; 1:75; 1:74; 1:73; 1:72; 1:71; 1:70; 1:69; 1:68; 1:67; 1:66; 1:65; 1:64; 1:63 1:62; 1:61; 1:60; 1:59; 1:58; 1:57; 1:56; 1:55; 1:54; 1:53; 1:52; 1:51; 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1.

The pharmaceutical compositions according to the invention containing the combinations of 1 and 2 are normally administered so that 1 and 2 are present together in doses of 0.01 to 10,000 µg, preferably from 0.1 to 8000 µg, more preferably from 1 to 5000 µg, better still from 2.5 to 2500 µg, more preferably from 10 to 1500 µg per single dose. For example, combinations of 1 and 2 according to the invention contain a quantity of 1' and endothelin antagonist 2 such that the total dosage per single dose is about 200 µg, 210 µg, 220 µg, 230 µg, 240 µg, 250 µg, 260 µg, 270 µg, 280 µg, 290 µg, 300 µg, 310 µg, 320 µg, 330 µg, 340 µg, 350 µg, 360 µg, 370 µg, 380 µg, 390 µg, 400 µg, 410 µg, 420 µg, 430 µg, 440 µg, 450 µg, 460 µg, 470 µg, 480 µg, 490 µg, 500 µg, 510 µg, 520 µg, 530 µg, 540 µg, 550 µg, 560 µg, 570 µg, 580 µg, 590 µg, 600 µg, 610 µg, 620 µg, 630 µg, 640 µg, 650 µg, 660 µg, 670 µg, 680 µg, 690 µg, 700 µg, 710 µg, 720 µg, 730 µg, 740 µg, 750 µg, 760 µg, 770 µg, 780 µg, 790 µg, 800 µg, 810 µg, 820 µg, 830 µg, 840 µg, 850 µg, 860 µg, 870 µg, 880 µg, 890 µg, 900 µg, 910 µg, 920 µg, 930 µg, 940 µg, 950 µg, 960 µg, 970 µg, 980 µg, 990 µg, 1000 µg, 1010 µg, 1020 µg, 1030 µg, 1040 µg, 1050 µg, 1060 µg, 1070 µg, 1080 µg, 1090 µg, 1100 µg, 1110 µg, 1120 µg, 1130 µg, 1140 µg, 1150 µg, 1160 µg, 1170 µg, 1180 µg, 1190 µg, 1200 µg, 1210 µg, 1220 µg, 1230 µg, 1240 µg, 1250 µg, 1260 µg, 1270 µg, 1280 µg, 1290 µg, 1300 µg, 1310 µg, 1320 µg, 1330 µg, 1340 µg, 1350 µg, 1360 µg, 1370 µg, 1380 µg, 1390 µg, 1400 µg, 1410 µg, 1420 µg, 1430 µg, 1440 µg, 1450 µg, 1460 µg, 1470 µg, 1480 µg, 1490 µg, 1500 µg, 1510 µg, 1520 µg, 1530 µg, 1540 µg, 1550 µg, 1560 µg, 1570 µg, 1580 µg, 1590 µg, 1600 µg, 1610 µg, 1620 µg, 1630 µg, 1640 µg, 1650 µg, 1660 µg, 1670 µg, 1680 µg, 1690 µg, 1700 µg, 1710 µg, 1720 µg, 1730 µg, 1740 µg, 1750 µg, 1760 µg, 1770 µg, 1780 µg, 1790 µg, 1800 µg, 1810 µg, 1820 µg, 1830 µg, 1840 µg, 1850 µg, 1860 µg, 1870 µg, 1880 µg, 1890 µg, 1900 µg, 1910 µg, 1920 µg, 1930 µg, 1940 µg, 1950 µg, 1960 µg, 1970 µg, 1980 µg, 1990 µg, 2000 µg or the like. The proposed dosages per single dose suggested above are not to be regarded as being restricted to the numerical values actually stated, but are intended only as examples of dosages. Of course, dosages which fluctuate around the above values in a range of about +/−5 µg are also covered by the values given above by way of example. In these dosage ranges the active substances 1' and 2 may be present in the weight ratios specified above.

For example, without restricting the scope of the invention thereto, the combinations of 1 and 2 according to the invention may contain a quantity of tiotropium 1' and endothelin antagonist 2 such that, in each individual dose, 5 µg of 1' and 100 µg of 2, 5 µg of 1' and 200 µg of 2, 5 µg of 1' and 300 µg of 2, 5 µg of 1' and 400 µg of 2, 5 µg of 1' and 500 µg of 2, 5 µg of 1' and 600 µg of 2, 5 µg of 1' and 700 µg of 2, 5 µg of 1' and 800 µg of 2, 5 µg of 1' and 900 µg of 2, 5 µg of 1' and 1000 µg of 2, 5 µg of 1' and 1500 µg of 2, 5 µg of 1' and 2000 µg of 2, 10 µg of 1' and 100 µg of 2, 10 µg of 1' and 200 µg of 2, 10 µg of 1' and 300 µg of 2, 10 μg of 1' and 400 μg of 2, 10 μg of 1' and 500 μg of 2, 10 μg of 1' and 600 μg of 2, 10 μg of 1' and 700 μg of 2, 10 μg of 1' and 800 μg of 2, 10 μg of 1' and 900 μg of 2, 10 μg of 1' and 1000 μg of 2, 10 μg of 1' and 1500 μg of 2, 10 μg of 1' and 200 μg of 2, 18 μg of 1' and 100 μg of 2, 18 μg of 1' and 200 μg of 2, 18 μg of 1' and 300 μg of 2, 18 μg of 1' and 400 μg of 2, 18 μg of 1' and 500 μg of 2, 18 μg of 1' and 600 μg of 2, 18 μg of 1' and 700 μg of 2, 18 μg of 1' and 800 μg of 2, 18 μg of 1' and 900 μg of 2, 18 μg of 1' and 1000 μg of 2, 18 μg of 1' and 1500 μg of 2, 18 μg of 1' and 2000 μg of 2, 20 μg of 1' and 100 μg of 2, 20 μg of 1' and 200 μg of 2, 20 μg of 1' and 300 μg of 2, 20 μg of 1' and 400 μg of 2, 20 μg of 1' and 500 μg of 2, 20 μg of 1' and 600 μg of 2, 20 μg of 1' and 700 μg of 2, 20 μg of 1' and 800 μg of 2, 20 μg of 1' and 900 μg of 2, 20 μg of 1' and 1000 μg of 2, 20 μg of 1' and 1500 μg of 2, 20 μg of 1' and 2000 μg of 2, 36 μg of 1' and 100 μg of 2, 36 μg of 1' and 200 μg of 2, 36 μg of 1' and 300 μg of 2, 36 μg of 1' and 400 μg of 2, 36 μg of 1' and 500 μg of 2, 36 μg of 1' and 600 μg of 2, 36 μg of 1' and 700 μg of 2, 36 μg of 1' and 800 μg of 2, 36 μg of 1' and 900 μg of 2, 36 μg of 1' and 1000 μg of 2, 36 μg of 1' and 1500 μg of 2, 36 μg of 1' and 2000 μg of 2, 40 μg of 1' and 100 μg of 2, 40 μg of 1' and 200 μg of 2, 40 μg of 1' and 300 μg of 2, 40 μg of 1' and 400 μg of 2, 40 μg of 1' and 500 μg of 2 or 40 μg of 1' and 600 μg of 2, 40 μg of 1' and 700 μg of 2, 40 μg of 1' and 800 μg of 2, 40 μg of 1' and 900 μg of 2, 40 μg of 1' and 1001 μg of 2, 40 μg of 1' and 1500 μg of 2, 40 μg of 1' and 2000 μg of 2 are administered.

If the active substance combination in which 1 denotes tiotropium bromide is used as the preferred combination of 1 and 2 according to the invention, the quantities of active substance 1' and 2 administered per single dose mentioned by way of example correspond to the following quantities of 1 and 2 administered per single dose: 6 μg of 1 and 100 μg of 2, 6 μg of 1 and 200 μg of 2, 6 μg of 1 and 300 μg of 2, 6 μg of 1 and 400 μg of 2, 6 μg of 1 and 500 μg of 2, 6 μg of 1 and 600 μg of 2, 6 μg of 1 and 700 μg of 2, 6 μg of 1 and 800 μg of 2, 6 μg of 1 and 900 μg of 2, 6 μg of 1 and 1000 μg of 2, 6 μg of 1 and 1500 μg of 2, 6 μg of 1 and 2000 μg of 2, 12 μg of 1 and 100 μg of 2, 12 μg of 1 and 200 μg of 2, 12 μg of 1 and 300 μg of 2, 12 μg of 1 and 400 μg of 2, 12 μg of 1 and 500 μg of 2, 12 μg of 1 and 600 μg of 2, 12 μg of 1 and 700 μg of 2, 12 μg of 1 and 800 μg of 2, 12 μg of 1 and 900 μg of 2, 12 μg of 1 and 1000 μg of 2, 12 μg of 1 and 1500 μg of 2, 12 μg of 1 and 2000 μg of 2, 21.7 μg of 1 and 100 μg of 2, 21.7 μg of 1 and 200 μg of 2, 21.7 μg of 1 and 300 μg of 2, 21.7 μg of 1and 400 μg of 2, 21.7 μg of 1 and 500 μg of 2, 21.7 μg of 1 and 600 μg of 2, 21.7 μg of 1 and 700 μg of 2, 21.7 μg of 1 and 800 μg of 2, 21.7 μg of 1 and 900 μg of 2, 21.7 μg of 1 and 1000 μg of 2, 21.7 μg of 1 and 1500 μg of 2, 21.7 μg of 1 and 2000 μg of 2, 24.1 μg of 1 and 100 μg of 2, 24.1 μg of 1 and 200 μg of 2, 24.1 μg of 1 and 300 μg of 2, 24.1 μg of 1 and 400 μg of 2, 24.1 μg of 1 and 500 μg of 2, 24.1 μg of 1 and 600 μg of 2, 24.1 μg of 1 and 700 μg of 2, 24.1 μg of 1 and 800 μg of 2, 24.1 μg of 1 and 900 μg of 2, 24.1 μg of 1 and 1000 μg of 2, 24.1 μg of 1 and 1500 μg of 2, 24.1 μg of 1 and 2000 μg of 2, 43.3 μg of 1 and 100 μg of 2, 43.3 μg of 1 and 200 μg of 2, 43.3 μg of 1 and 300 μg of 2, 43.3 μg of 1 and 400 μg of 2, 43.3 μg of 1 and 500 μg of 2, 43.3 μg of 1 and 600 μg of 2, 43.3 μg of 1 and 700 μg of 2, 43.3 μg of 1 and 800 μg of 2, 43.3 μg of 1 and 900 μg of 2, 43.3 μg of 1 and 10,00 μg of 2, 43.3 μg of 1 and 1500 μg of 2, 43.3 μg of 1 and 2000 μg of 2, 48.1 μg of 1 and 1100 μg of 2, 48.1 μg of 1 and 200 μg of 2, 48.1 μg of 1 and 300 μg of 2, 48.1 μg of 1 and 400 μg of 2, 48.1 μg of 1 and 500 μg of 2, 48.1 μg of 1 and 600 μg of 2, 48.1 μg of 1 and 700 μg of 2, 48.1 μg of 1 and 800 μg of 2, 48.1 μg of 1 and 900 μg of 2, 48.1 μg of 1 and 1000 μg of 2, 48.1 μg of 1 and 1500 μg of 2 or 48.1 μg of 1 and 200 μg of 2.

If the active substance combination in which 1 is tiotropium bromide monohydrate is used as the preferred combination of 1 and 2 according to the invention, the quantities of 1' and 2 administered per single dose specified by way of example hereinbefore correspond to the following quantities of 1 and 2 administered per single dose: 6.2 μg of 1 and 100 μg of 2, 6.2 μg of 1 and 200 μg of 2, 6.2 μg of 1 and 300 μg of 2, 6.2 μg of 1 and 400 μg of 2, 6.2 μg of 1 and 500 μg of 2, 6.2 μg of 1 and 600 μg of 2, 6.2 μg of 1 and 700 μg of 2, 6.2 μg of 1 and 800 μg of 2, 6.2 μg of 1 and 900 μg of 2, 6.2 μg of 1 and 1000 μg of 2, 6.2 μg of 1 and 1500 μg of 2, 6.2 μg of 1 and 2000 μg of 2, 12.5 μg of 1 and 100 μg of 2, 12.5 μg of 1 and 200 μg of 2, 12.5 μg of 1 and 300 μg of 2, 12.5 μg of 1 and 400 μg of 2, 12.5 μg of 1 and 500 μg of 2, 12.5 μg of 1 and 600 μg of 2, 12.5 μg of 1 and 700 μg of 2, 12.5 μg of 1 and 800 μg of 2, 12.5 μg of 1 and 900 μg of 2, 12.5 μg of 1 and 1000 μg of 2, 12.5 μg of 1 and 1500 μg of 2, 12.5 μg of 1 and 2000 μg of 2, 22.5 μg of 1 and 100 μg of 2, 22.5 μg of 1 and 200 μg of 2, 22.5 μg of 1 and 300 μg of 2, 22.5 μg of 1 and 400 μg of 2, 22.5 μg of 1 and 500 μg of 2, 22.5 μg of 1 and 600 μg of 2, 22.5 μg of 1 and 700 μg of 2, 22.5 μg of 1 and 800 μg of 2, 22.5 μg of 1 and 900 μg of 2, 22.5 μg of 1 and 10,00 μg of 2, 22.5 μg of 1 and 1500 μg of 2, 22.5 μg of 1 and 2000 μg of 2, 25 μg of 1 and 10 μg of 2, 25 μg of 1 and 200 μg of 2, 25 μg of 1 and 300 μg of 2, 25 μg of 1 and 400 μg of 2, 25 μg of 1 and 500 μg of 2, 25 μg of 1 and 600 μg of 2, 25 μg of 1 and 700 μg of 2, 25 μg of 1 and 800 μg of 2, 25 μg of 1 and 900 μg of 2, 25 μg of 1 and 1000 μg of 2, 25 μg of 1 and 1500 μg of 2, 25 μg of 1 and 2000 μg of 2, 45 μg of 1 and 100 μg of 2, 45 μg of 1 and 200 μg of 2, 45 μg of 1 and 300 μg of 2, 45 μg of 1 and 400 μg of 2, 45 μg of 1 and 500 μg of 2, 45 μg of 1 and 600 μg of 2, 45 μg of 1 and 700 μg of 2, 45 μg of 1 and 800 μg of 2, 45 μg of 1 and 900 μg of 2, 45 μg of 1 and 1000 μg of 2, 45 μg of 1 and 1500 μg of 2, 45 μg of 1 and 2000 μg of 2, 50 μg of 1 and 100 μg of 2, 50 μg of 1 and 200 μg of 2, 50 μg of 1 and 300 μg of 2, 50 μg of 1 and 400 μg of 2, 50 μg of 1 and 500 μg of 2, 50 μg of 1 and 600 μg of 2, 50 μg of 1 and 700 μg of 2, 50 μg of 1 and 800 μg of 2, 50 μg of 1 and 900 μg of 2, 50 μg of 1 and 1000 μg of 2, 50 μg of 1 and 1500 μg of 2 or 50 μg of 1 and 200 μg of 2.

The active substance combinations of 1 and 2 according to the invention are preferably administered by inhalation or by nasal application. For this purpose, ingredients 1 and 2 have to be made available in inhalable forms. Inhalable preparations include inhalable powders, propellant-containing metering aerosols or propellant-free inhalable solutions. Inhalable powders according to the invention containing the combination of active substances 1 and 2 may consist of the active substances on their own or of a mixture of the active substances with physiologically acceptable excipients. Within the scope of the present invention, the term propellant-free inhalable solutions also includes concentrates or sterile inhalable solutions ready for use. The preparations according to the invention may contain the combination of active substances 1 and 2 either together in one formulation or in two separate formulations. These formulations which may be used within the scope of the present invention are described in more detail in the next part of the specification.

A) Inhalable Powder Containing the Combinations of Active Substances 1 and 2 According to the Invention The inhalable powders according to the invention may contain 1 and 2 either on their own or in admixture with suitable physiologically acceptable excipients. If the active substances 1 and 2 are present in admixture with physiologically acceptable excipients, the following physiologically acceptable excipients may be used to prepare these inhalable powders according to the invention:

monosaccharides (e.g. glucose or arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 $\mu$m, preferably between 10 and 150 $\mu$m, most preferably between 15 and 80 $\mu$m. It may sometimes seem appropriate to add finer excipient fractions with an average particle size of 1 to 9 $\mu$m to the excipients mentioned above. These finer excipients are also selected from the group of possible excipients listed hereinbefore. Finally, in order to prepare the inhalable powders according to the invention, micronised active substance 1 and 2, preferably with an average particle size of 0.5 to 10 $\mu$m, more preferably from 1 to 5 $\mu$m, is added to the excipient mixture. Processes for producing the inhalable powders according to the invention by grinding and micronising and by finally mixing the ingredients together are known from the prior art. The inhalable powders according to the invention may be prepared and administered either in the form of a single powder mixture which contains both 1 and 2 or in the form of separate inhalable powders which contain only 1 or 2.

The inhalable powders according to the invention may be administered using inhalers known from the prior art. Inhalable powders according to the invention which contain a physiologically acceptable excipient in addition to 1 and 2 may be administered, for example, by means of inhalers which deliver a single dose from a supply using a measuring chamber as described in U.S. Pat. No. 4,570,630A, or by other means as described in DE 36 25 685 A. The inhalable powders according to the invention which contain 1 and 2 optionally combined with a physiologically acceptable excipient may be administered for example with an inhaler known by the name Turbuhaler®, for example with inhalers as disclosed in EP 237507 A, for example. Preferably, the inhalable powders according to the invention which contain physiologically acceptable excipient in addition to 1 and 2 are packed into capsules (to produce so-called inhalettes) which are used in inhalers as described, for example, in WO 94/28958.

Figure 1:
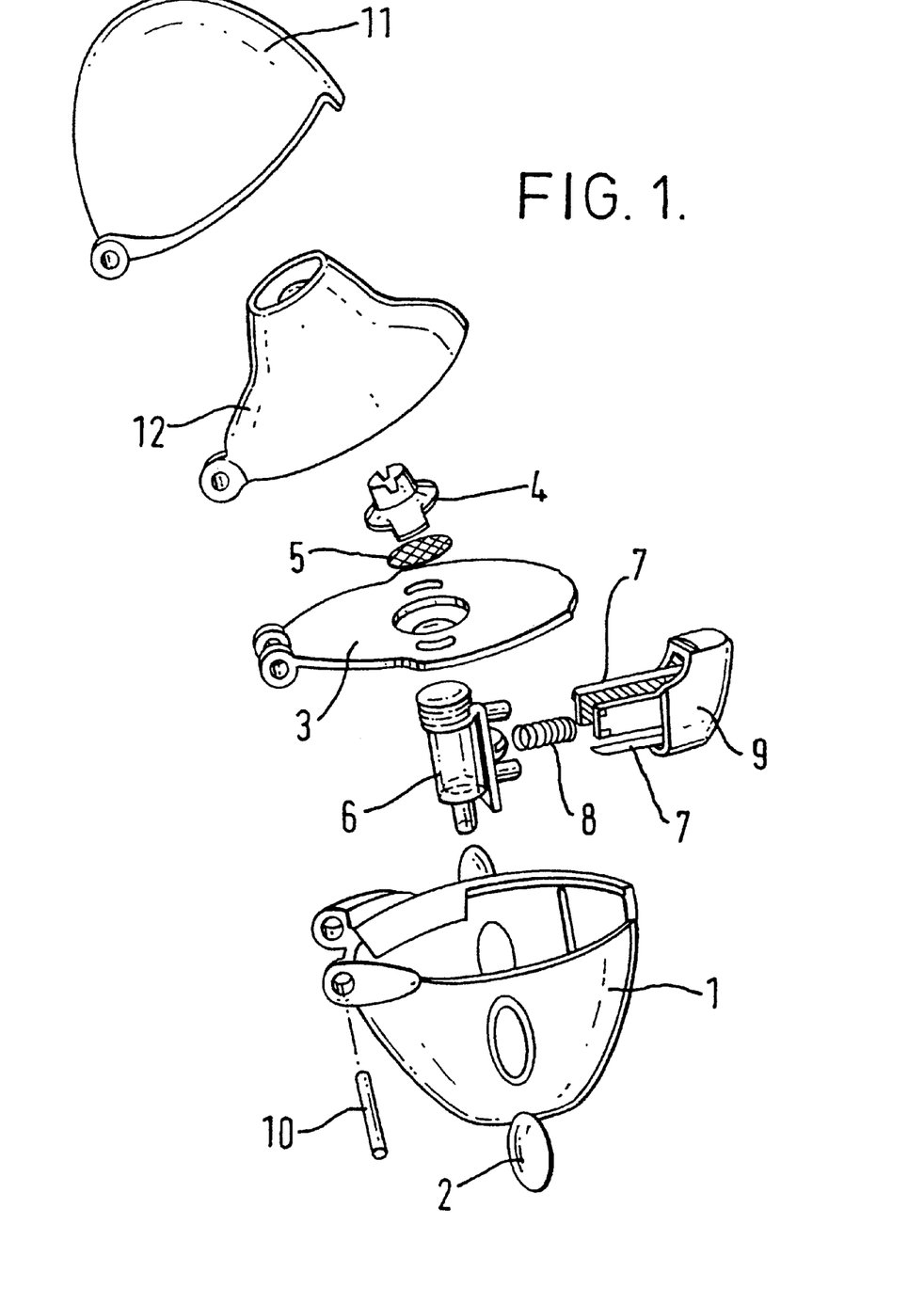
FIG. 1 shows an exploded view of a device to enable inhalation of a powdered medicament.

A particularly preferred inhaler for administering the pharmaceutical combination according to the invention in inhalettes is shown in FIG. 1.

This inhaler (Handyhaler) for inhaling powdered pharmaceutical compositions from capsules is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut.

If the inhalable powders according to the invention are packed into capsules (inhalers) for the preferred use described above, the quantities packed into each capsule should be 1 to 30 mg, preferably 3 to 20 mg, more particularly 5 to 10 mg of inhalable powder per capsule. These capsules contain, according to the invention, either together or separately, the doses of 1' and 2 mentioned hereinbefore for each single dose.

B) Propellant Gas-driven Inhalation Aerosols Containing the Combinations of Active Substances 1 and 2 According to the Invention Inhalation aerosols containing propellant gas according to the invention may contain substances 1 and 2 dissolved in the propellant gas or in dispersed form. 1 and 2 may be present in separate formulations or in a single preparation, in which 1 and 2 are either both dissolved, both dispersed or only one component is dissolved and the other is dispersed. The propellant gases which may be used to prepare the inhalation aerosols according to the invention are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The propellant gases mentioned above may be used on their own or in mixtures thereof. Particularly preferred propellant gases are halogenated alkane derivatives selected from TG134a (1,1,1,2-tetrafluoroethane) and TG227(1,1,1,2,3,3,3-heptafluoropropane) and mixtures thereof.

The propellant-driven inhalation aerosols according to the invention may also contain other ingredients such as co-solvents, stabilisers, surfactants, antioxidants, lubricants and pH adjusters. All these ingredients are known in the art.

The inhalation aerosols containing propellant gas according to the invention may contain up to 5 wt.- % of active substance 1 and/or 2. Aerosols according to the invention contain, for example, 0.002 to 5 wt.- %, 0.01 to 3 wt.- %, 0.015 to 2 wt.- %, 0.1 to 2 wt.- %, 0.5 to 2 wt.- % or 0.5 to 1.5 wt.- % of active substance 1 and/or 2. If the active substances 1 and/or 2 are present in dispersed form, the particles of active substance preferably have an average particle size of up to 10 $\mu$m, preferably from 0.1 to 5 $\mu$m, more preferably from 1 to 5 $\mu$m.

The propellant-driven inhalation aerosols according to the invention mentioned above may be administered using inhalers known in the art (MDIs=metered dose inhalers). Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterised in that they contain the propellant gas-containing aerosols described above according to the invention. The present invention also relates to cartridges which when fitted with a suitable valve can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C) Propellant-free Inhalable Solutions or Suspensions Containing the Combinations of Active Substances 1 and 2 According to the Invention It is particularly preferred to use the active substance combination according to the invention in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 and 2, separately or together, are adjusted to a pH of 2 to 7, preferably 2 to 5, using suitable acids. The pH may be adjusted using acids selected from inorganic or organic acids. Examples of suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

According to the invention, the addition of editic acid (EDTA) or one of the known salts thereof, sodium edetate, as stabiliser or complexing agent is unnecessary in the present formulation. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

The preservatives mentioned above are preferably present in concentrations of up to 50 mg/100 ml, more preferably between 5 and 20 mg/100 ml.

Preferred formulations contain, in addition to the solvent water and the combination of active substances 1 and 2, only benzalkonium chloride and sodium edetate. In another preferred embodiment, no sodium edetate is present.

The propellant-free inhalable solutions according to the invention are administered in particular using inhalers of the kind which are capable of nebulising a small amount of a liquid formulation in the therapeutic dose within a few seconds to produce an aerosol suitable for therapeutic inhalation. Within the scope of the present invention, preferred inhalers are those in which a quantity of less than 100 $\mu$L, preferably less than 50 $\mu$L, more preferably between 10 and 30 $\mu$L of active substance solution can be nebulised in preferably one spray action to form an aerosol with an average particle size of less than 20 $\mu$m, preferably less than 10 $\mu$m, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf. in particular FIGS. 6*a* and 6*b*). The nebulisers (devices) described therein are known by the name Respimat®.

This nebuliser (Respimat®) can advantageously be used to produce the inhalable aerosols according to the invention containing the combination of active substances 1 and 2. Because of its cylindrical shape and handy size of less than 9 to 15 cm long and 2 to 4 cm wide, this device can be carried at all times by the patient. The nebuliser sprays a defined volume of pharmaceutical formulation using high pressures through small nozzles so as to produce inhalable aerosols.

The preferred atomiser essentially consists of an upper housing part, a pump housing, a nozzle, a locking mechanism, a spring housing, a spring and a storage container, characterised by

- a pump housing which is secured in the upper housing part and which comprises at one end a nozzle body with the nozzle or nozzle arrangement,
- a hollow plunger with valve body,
- a power takeoff flange in which the hollow plunger is secured and which is located in the upper housing part,
- a locking mechanism situated in the upper housing part,
- a spring housing with the spring contained therein, which is rotatably mounted on the upper housing part by means of a rotary bearing,
- a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 to 60 Mpa (about 50 to 600 bar), preferably 10 to 60 Mpa (about 100 to 600 bar) on the fluid, the measured amount of active substance solution, at its high pressure end at the moment when the spring is actuated. Volumes of 10 to 50 microlitres are preferred, while volumes of 10 to 20 microlitres are particularly preferred and a volume of 15 microlitres per spray is most particularly preferred.

The valve body is preferably mounted at the end of the hollow plunger facing the valve body.

The nozzle in the nozzle body is preferably microstructured, i.e. produced by microtechnology. Microstructured valve bodies are disclosed for example in WO-94/07607; reference is hereby made to the contents of this specification, particularly FIG. 1 therein and the associated description.

The valve body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

Figure 2A:
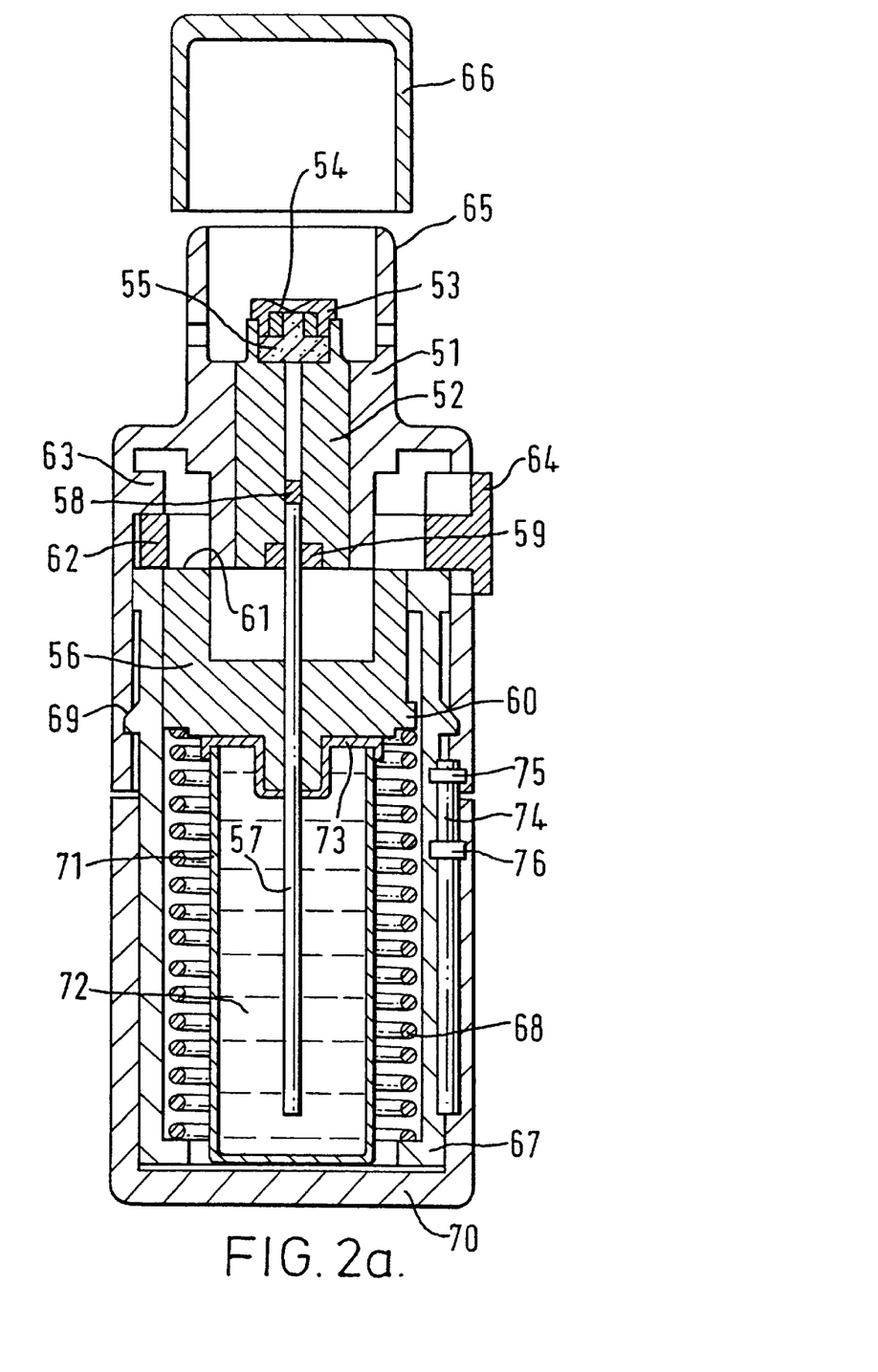
FIG. 2a shows a longitudinal cross-sectional view of a nebulizer with its spring biased.
Figure 2B:
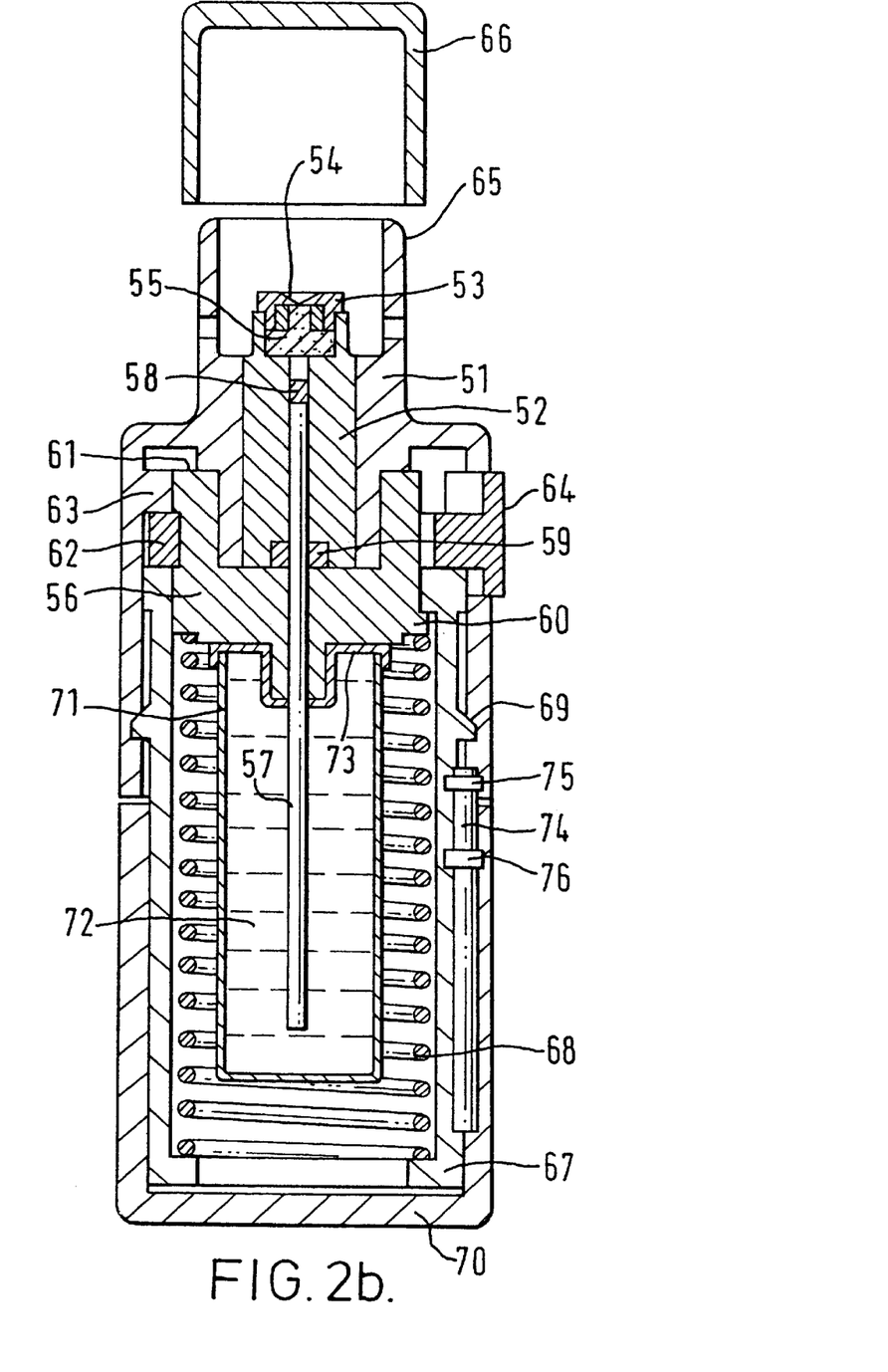
FIG. 2b shows a longitudinal cross-sectional view of a nebulizer with its spring relaxed.

The liquid pharmaceutical preparation strikes the nozzle body with an entry pressure of up to 600 bar, preferably 200 to 300 bar, and is atomised into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g. a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomiser axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomiser; this causes the deformable ring to deform in the annual plane. Details of the construction of the locking mechanism are given in WO 97/20590.

The lower housing part is pushed axially over the spring housing and covers the mounting, the drive of the spindle and the storage container for the fluid.

When the atomiser is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomised may be pushed into the atomiser one after another and used in succession. The storage container contains the aqueous aerosol preparation according to the invention.

The atomising process is initiated by pressing gently on the actuating button. As a result, the locking mechanism opens up the path for the power takeoff member. The biased spring pushes the plunger into the cylinder of the pump housing. The fluid leaves the nozzle of the atomiser in atomised form.

Further details of construction are disclosed in PCT Applications WO 97/12683 and WO 97/20590, to which reference is hereby made.

The components of the atomiser (nebuliser) are made of a material which is suitable for its purpose. The housing of the atomiser and, if its operation permits, other parts as well are preferably made of plastics, e.g. by injection moulding. For medicinal purposes, physiologically safe materials are used.

FIGS. 2*a*/*b* attached to this patent application, which are identical to FIGS. 6*a*/*b* of WO 97/12687, show the nebuliser (Respimat®) which can advantageously be used for inhaling the aqueous aerosol preparations according to the invention.

FIG. 2*a* shows a longitudinal section through the atomiser with the spring biased while FIG. 2*b* shows a longitudinal section through the atomiser with the spring relaxed.

The upper housing part (51) contains the pump housing (52) on the end of which is mounted the holder (53) for the atomiser nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomised. The storage container is sealed off by the stopper (73) through which the hollow plunger projects into the storage container and is immersed at its end in the fluid (supply of active substance solution).

The spindle (74) for the mechanical counter is mounted in the covering of the spring housing. At the end of the spindle facing the upper housing part is the drive pinion (75). The slider (76) sits on the spindle.

The nebuliser described above is suitable for nebulising the aerosol preparations according to the invention to produce an aerosol suitable for inhalation.

If the formulation according to the invention is nebulised using the method described above (Respimat®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation.

However, the formulation according to the invention may also be nebulised by means of inhalers other than those described above, e.g. jet stream inhalers or other stationary nebulisers.

Accordingly, in a further aspect, the invention relates to pharmaceutical formulations in the form of propellant-free inhalable solutions or suspensions as described above combined with a device suitable for administering these formulations, preferably in conjunction with the Respimat®). Preferably, the invention relates to propellant-free inhalable solutions or suspensions characterised by the combination of active substances 1 and 2 according to the invention in conjunction with the device known by the name Respimat®. In addition, the present invention relates to the above-mentioned devices for inhalation, preferably the Respimat®, characterised in that they contain the propellant-free inhalable solutions or suspensions according to the invention as described hereinbefore.

Inhalable solutions which contain the active substances 1 and 2 in a single preparation are preferred according to the invention. The term preparation also includes those which contain both ingredients 1 and 2 in two-chamber cartridges as disclosed for example in WO 00/23037. Reference is hereby made to this publication in its entirety.

The propellant-free inhalable solutions or suspensions according to the invention may take the form of concentrates or sterile inhalable solutions or suspensions ready for use, as well as the above-mentioned solutions and suspensions designed for use in a Respimat®. Formulations ready for use may be produced from the concentrates, for example, by the addition of isotonic saline solutions. Sterile formulations ready for use may be administered using energy-operated fixed or portable nebulisers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterised in that the device is an energy-operated free-standing or portable nebuliser which produces inhalable aerosols by means of ultrasound or compressed air by the Venturi principle or other methods.

The Examples which follow serve to illustrate the present invention in more detail without restricting the scope of the invention to the following embodiments by way of example.

STARTING MATERIALS

Tiotropium Bromide

The tiotropium bromide used in the following formulations examples may be obtained as described in European Patent Application 418 716 A1.

In order to prepare the inhalable powders according to the invention, crystalline tiotropium bromide monohydrate may also be used. This crystalline tiotropium bromide monohydrate may be obtained by the method described below.

15.0 kg of tiotropium bromide are placed in 25.7 kg of water in a suitable reaction vessel. The mixture is heated to 80–90° C. and stirred at constant temperature until a clear solution is formed. Activated charcoal (0.8 kg) moistened with water is suspended in 4.4 kg of water, this mixture is added to the solution containing the tiotropium bromide and the resulting mixture is rinsed with 4.3 kg of water. The mixture thus obtained is stirred for at least 15 minutes at 80–90° C. and then filtered through a heated filter into an apparatus preheated to an external temperature of 70° C. The filter is rinsed with 8.6 kg of water. The contents of the apparatus are cooled at 3–5° C. for every 20 minutes to a temperature of 20–25° C. The apparatus is cooled further to 10–15° C. using cold water and crystallisation is completed by stirring for at least another hour. The crystals are isolated using a suction filter dryer, the crystal slurry isolated is washed with 9 litres of cold water (10–15° C.) and cold acetone (10–15° C.). The crystals obtained are dried at 25° C. in a nitrogen current over a period of 2 hours.

Yield: 13.4 μg of tiotropium bromide monohydrate (86% of theory).

The crystalline tiotropium bromide monohydrate thus obtained is micronised by known methods in order to prepare the active substance in the form of the average particle size corresponding to the specifications according to the invention.

EXAMPLES OF FORMULATIONS

A) Inhalable Powders

1)

| Ingredients | μg per capsule |
|---|---|
| Tiotropium bromide | 21.7 |
| Endothelin antagonist 2 | 270 |
| Lactose | 4708.3 |
| Total | 5000 |

2)

| Ingredients | μg per capsule |
|---|---|
| Tiotropium bromide | 21.7 |
| Endothelin antagonist 2 | 450 |
| Lactose | 4528.3 |
| Total | 5000 |

3)

| Ingredients | μg per capsule |
|---|---|
| Tiotropium bromide × $H_2O$ | 22.5 |
| Endothelin antagonist 2 | 495 |
| Lactose | 4482.5 |
| Total | 5000 |

4)

| Ingredients | μg per capsule |
|---|---|
| Tiotropium bromide | 21.7 |
| Endothelin antagonist 2 | 1400 |
| Lactose | 3578.3 |
| Total | 5000 |

5)

| Ingredients | μg per capsule |
|---|---|
| Ipratropium bromide | 40 |
| Endothelin antagonist 2 | 2000 |
| Lactose | 2960 |
| Total | 5000 |

6)

| Ingredients | μg per capsule |
|---|---|
| Ipratropium bromide | 20 |
| Endothelin antagonist 2 | 495 |
| Lactose | 4485 |
| Total | 5000 |

B) Propellant Gas-containing Aerosols for Inhalation

1) Suspension Aerosol

| Ingredients | wt.-% |
|---|---|
| Tiotropium bromide | 0.015 |
| Endothelin antagonist 2 | 1.2 |
| Soya lecithin | 0.3 |
| TG 134a:TG227 = 2:3 | ad 100 |

2) Suspension Aerosol

| Ingredients | wt.-% |
|---|---|
| Ipratropium bromide | 0.015 |
| Endothelin antagonist 2 | 1.2 |
| soya lecithin | 0.3 |
| TG 134a:TG227 = 2:3 | ad 100 |

3) Suspension Aerosol

| Ingredients | wt.-% |
|---|---|
| Tiotropium bromide | 0.029 |
| Endothelin antagonist 2 | 1.4 |
| Absolute ethanol | 0.5 |
| Isopropyl myristate | 0.1 |
| TG 227 | ad 100 |

4) Suspension Aerosol

| Ingredients | wt.-% |
|---|---|
| Ipratropium bromide | 0.029 |
| Endothelin antagonist 2 | 1.4 |
| Absolute ethanol | 0.5 |
| Isopropyl myristate | 0.1 |
| TG 227 | ad 100 |

What is claimed is:

1. An inhalable powder which comprises at least two active drug substances which drug substances are a salt of tiotropium and one or more endothelin antagonists, together with a pharmaceutically acceptable excipient selected from glucose, arabinose, lactose, saccharose or maltose.

2. The inhalable powder as recited in claim 1 wherein the salt of tiotropium is the chloride, bromide, iodide, methane sulphonate or paratoluene sulphonate salt.

3. The inhalable powder as recited in claim 2 wherein the salt of tiotropium is the bromide salt.

4. The inhalable powder as recited in claim 1 wherein the endothelin antagonist is selected from tezosentan, bosentan, enrasentan, sixtasentan, T-0201, BMS-193884, K-8794, PD-156123, PD-156707, PD-160874, PD-180988, S-0139 and ZD-1611.

5. The inhalable powder as recited in claim 4 wherein the endothelin antagonist is selected from tezosentan, bosentan, enrasentan, sixtasentan, T-0201 and BMS-193884.

6. The inhalable powder as recited in claim 1 wherein the weight ratio of tiotropium salt to endothelin antagonist is about 1:300 to about 50:1.

7. The inhalable powder as recited in claim 6 wherein the weight ratio of anticholinergic substance to endothelin antagonist is about 1:250 to about 40:1.

8. A method for the treatment of asthma which method comprises administering the inhalable powder as recited in claim 1.

9. A method for the treatment of chronic obstructive pulmonary disease which method comprises administering the inhalable powder as recited in claim 1.

* * * * *